(12) United States Patent
Bjursten et al.

(10) Patent No.: US 7,547,471 B2
(45) Date of Patent: Jun. 16, 2009

(54) MATERIAL FOR IMPLANTATION

(75) Inventors: Lars M. Bjursten, Limhamn (SE); John A. Frangos, La Jolla, CA (US)

(73) Assignee: La Jolla Bioengineering Institute, La Jolla, CA (US)

( * ) Notice: Subject to any disclaimer, the term of this patent is extended or adjusted under 35 U.S.C. 154(b) by 647 days.

(21) Appl. No.: 10/503,405

(22) PCT Filed: Jan. 31, 2003

(86) PCT No.: PCT/SE03/00163

§ 371 (c)(1),
(2), (4) Date: Jul. 30, 2004

(87) PCT Pub. No.: WO03/063925

PCT Pub. Date: Aug. 7, 2003

(65) Prior Publication Data

US 2005/0074602 A1    Apr. 7, 2005

(30) Foreign Application Priority Data

Jan. 31, 2002    (SE)    .................................. 0200269

(51) Int. Cl.
*A61F 2/02* (2006.01)
*B32B 27/00* (2006.01)
*B32B 27/40* (2006.01)
*B32B 27/32* (2006.01)

(52) U.S. Cl. .................... 428/195.1; 424/400; 424/421; 424/422; 424/423; 427/2.27; 604/382; 428/334; 428/423.1; 428/447; 428/523; 623/11.11

(58) Field of Classification Search ................ 428/357, 428/377, 195.1, 376, 334, 423.1, 447, 523; 501/18; 424/400, 421, 422; 427/2.27; 604/382; 205/112; 623/11.11
See application file for complete search history.

(56) References Cited

U.S. PATENT DOCUMENTS

| 4,846,834 | A |   | 7/1989 | Von Recum et al. |
| 5,468,562 | A |   | 11/1995 | Farivar et al. |
| 6,057,031 | A | * | 5/2000 | Breme et al. ................ 428/336 |
| 6,110,204 | A | * | 8/2000 | Lazarov et al. ........... 623/11.11 |
| 2008/0319292 | A1 | * | 12/2008 | Say et al. .................... 600/347 |

FOREIGN PATENT DOCUMENTS

| WO | WO 98/17199 A2 | 4/1998 |
| WO | WO9817199 A2 * | 4/1998 |
| WO | WO 99/47471 A1 | 9/1999 |
| WO | WO0004389 A2 * | 1/2000 |

OTHER PUBLICATIONS

Albrektsson, T., et al. (1983). "The interface zone of inorganic implants in vivo: Titanium implants in bone." Annals of Biomedical Engineering 11: 1-27.
Cuzzocrea, S., et al. (2000). "Beneficial effects of peroxynitrite decomposition catalyst in a rat model of splanchinic artery occulsion and reperfusion." FASEB Journal 14(N9): 1061-1072.
Glowinski, J., et al. (1997). "Activity and distribution of superoxide dismutase in the layers of polyester grafts." European Surgical Research 29: 368-374.
Hukkanen, M., et al. (1997). "Aseptic loosening of total hip replacement. Macrophage expression of inducible nitric oxide synthase and cyclo-oxygenase-2, together with peroxynitrite formation, as a possible mechanism for early prosthesis failure." Journal of Bone and Joint Surgery. British vol. 79(3): 467-474.
Hukkanen, M., et al. (1998). "Nitric oxide in the local host reaction to total hip replacement." Clinical Orthopaedics and Related Research 352: 53-62.
Johansson, A; et al. (1999) Material and design in haematogenous implant-associated infections in a rabbit model. Injury 30(10):651-7.
Misko, T. P., et al. (1998). "Characterization cytoprotective action of peroxynitrite decomposition catalysts." Journal of Biological Chemistry 273(25): 15646-15653.
Salvemini, D., et al. (1999). "Protective effects of a superoxide dismutase mimetic and peroxynitrite decomposition catalysts in endotoxin-induced intestinal damage." British Journal of Pharmacology 127(N3): 685-692.
Suzuki, R. and J. A. Frangos (2000). "Inhibition of inflammatory species by titanium surfaces." Clinical Orthopaedics and Related Research 372: 280-289.
Towler, M.R. (2000) "Novel Processing of Hydroxyapatite-Zirconia Composites Using Nano-sized Particles." Journal of Materials Science Letters 19: 2209-11.
Udipi, K., et al. (2000). "Modification of inflammatory response to implanted biomedical materials in vivo by surface bound superoxide dismutase mimics." Journal of Biomedical Materials Research 51: 549-560.
Hayden, B. et al., "Electrode coatings from sprayed titanium dioxide nanoparticles—behaviour in NaOH solutions" Electrochemistry Communications 3 (2001) pp. 390-394.

* cited by examiner

*Primary Examiner*—Callie E Shosho
*Assistant Examiner*—Prashant J Khatri
(74) *Attorney, Agent, or Firm*—O'Melveny & Myers LLP

(57) ABSTRACT

The present invention relates to a material for implantation, which is characterised in that the surface of the material partially comprises at least one area of an inorganic, catalytical substance for improved biocompatibility of the material. Methods for the manufacturing of the material for implantation and the use thereof is also disclosed.

7 Claims, 3 Drawing Sheets

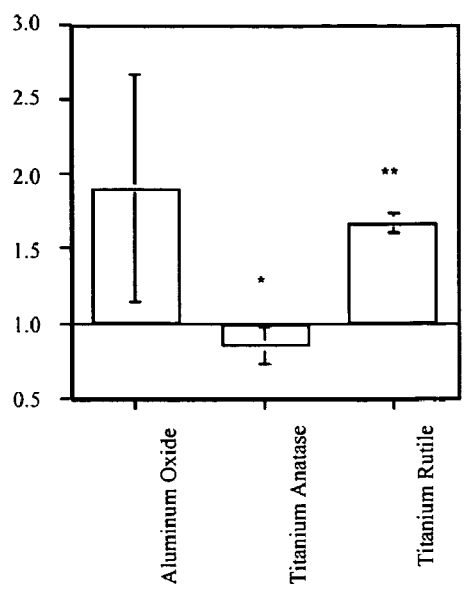
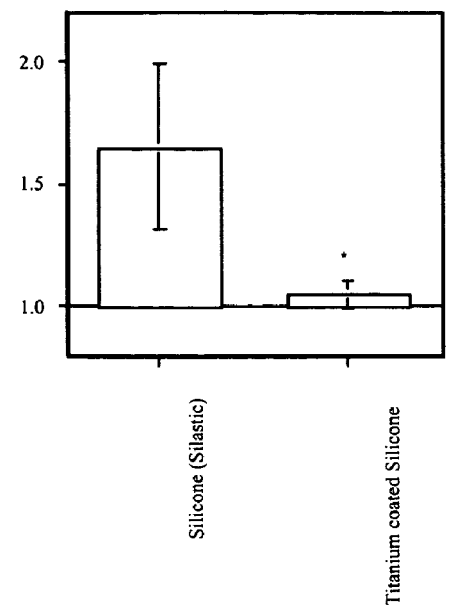
\* p < 0.05 vs Aluminum Oxide
(Student-Newman-Keuls Test)
\*\* p < 0.05 vs Titanium Anatase (Student-Newman-Keuls Test)
\* p < 0.05 vs Silicone
(Student-T test)
Fig. 1A
Fig. 1B

MATERIAL FOR IMPLANTATION

GOVERNMENT INTERESTS

This invention was made with government support under EB00823 and DK065457 awarded by the National Institute of Health. The government has certain rights in the invention.

This is a national stage application of international application no. PCT/SE03/00163, filed Jan. 31, 2003, which in turn claims priority to Swedish Application No. 0200269-9, filed Jan. 31, 2002. All of the above applications are expressly incorporated herein by reference in their entirety.

FIELD OF THE INVENTION

The present invention relates to a material for implantation, a method of manufacturing a material for implantation and use of a material for implantation.

BACKGROUND OF THE INVENTION

Tissue reaction after implantation of a foreign material or device in the body follows a general pattern, independent of the material used. The initial inflammatory response to an implant consists of acute vasculature changes induced by surgical trauma. Neutrophils migrate to the wound site after this trauma. Migration of monocytes follows. These monocytes then differentiate into macrophages. The macrophage can be viewed as a control cell in the inflammatory response, playing a central role in the interaction of inflammatory mediators.

Titanium is a biomaterial that exhibits good biocompatibility and minimal inflammatory response following implantation. Early studies observed that titanium bone implants in animals were well accepted when compared to other metals. Other studies have shown that titanium evokes less tissue reaction in rabbit muscle as compared to other metals. Clinical trials performed in 1965 indicated a 90% success rate for titanium dental implants (Albrektsson, Branemark et al. 1983). Titanium is used extensively in restorative surgery, particularly as a bone-anchoring and joint-replacement material. Further, there is experimental evidence that titanium as an implant material is less susceptible to infections than stainless steel (Johansson et al., 1999).

Given the normal initial tissue response to titanium, it would be expected that titanium implants would produce a typical inflammatory response. Macrophages near titanium implants, however, do not appear activated and leukocytes associated with titanium implants are less responsive. Although titanium is widely used as an implant material, the mechanisms of its superior biocompatibility are currently unknown.

One explanation is that the surface of titanium implants down regulate the inflammatory response (whose initiation is inevitable) by preventing its prolongation, thereby reducing the overall tissue response and allowing healing to proceed. Titanium readily forms a stable surface layer of oxide upon exposure to air, predominantly consisting of titanium dioxide, $TiO_2$. This oxide layer of titanium is the surface encountered by inflammatory cells after insertion of the implant. It has been proposed that the oxide layer plays a fundamental role in tissue response (Albrektsson, Branemark et al. 1983) and the oxide layer has been regarded as important because of its corrosion resistance properties.

Polymer and glass surfaces have been coated with titanium. The reasons for these procedures are to achieve methodological advantages when evaluating the responses of biomolecules, cells and tissues to titanium. By coating a glass surface with metallic titanium an extremely flat surface suitable for spectroscopy may be obtained. By coating a polymeric material like epoxy resin or polycarbonate you allow for sectioning of the coated implant material in situ together with the adjacent tissue as the solid metal is only sectional through expensive and time consuming grinding techniques that also restrict the subsequent microscopic analysis.

Devices have also been coated with metallic titanium to benefit from the perceived but not defined good biocompatibility of titanium. An example of many such applications is described in PCT/SE93/00924.

Current manufacturing technology can provide a wide range of materials with various physical properties but most cannot be utilized as biomaterials because of issues of biocompatibility. The response of cells of foreign materials placed within the body can lead to inflammation and rejection unless the implanted device is made of a relatively small number of materials which include titanium and Ti-6Al-4V alloy. This small selection of biocompatible materials limits the design and development of devices which can be implanted in the body.

Since titanium is a metal it does not have the wide variation of physical characteristics which polymers can achieve. Yield strength, elastic modulus and elongation are some of the factors which can be varied more easily in polymeric materials compared to metallic materials.

Also, titanium is not suitable in biosensors. They have to be constructed with other materials than titanium to achieve their function. Many such sensors must have semi permeable membranes to allow the exchange of molecules to be monitored.

SUMMARY OF THE INVENTION

The object of the present invention is to give materials for implantation the superior catalytic properties of titanium, without having to rely on the inherent limitations of titanium.

In one aspect of the invention this object is full filled by a material for implantation, characterised in that the surface of the material partially comprises at least one area of an inorganic, catalytic substance for improved biocompatibility of the material.

Thus, the present invention will allow a wider range of choices when selecting biomaterials and permit medical engineers to choose the precise material best suited for the needs of a particular implant. The use of the present invention will also improve the biocompatibility of medical devices already in use. One important object is to obtain the right pattern with respect to the distribution of catalytic areas over the surface, ie the spacing between adjacent catalytic areas.

In one embodiment of the material for implantation according to the invention, the distance between the areas of inorganic, catalytic substance is from 10 nm to 10 µm.

In another embodiment of the material for implantation according to the invention, the surface of the material is partially covered by a layer of the inorganic, catalytic substance patterned into an array of areas and in yet another embodiment the layer has a thickness of from 1 nm to 100 µm, preferably from 10 to 100 nm.

The entire surface cannot in many instances be coated with the catalytic thin film, for example, permeable membranes in implantable glucose sensors. The membrane needs to remain permeable to perform its sensing function and coating the entire surface is not an option. Coating the surface with a catalytic thin film patterned into an array of areas will resolve this problem.

In another embodiment of the material for implantation according to the invention, the inorganic, catalytic substance is comprised throughout the material as particles, forming the at least one area of inorganic, catalytic substance on the surface and in yet another embodiment the particles have a size in the range from 1 to 500 nm, preferably from 10 to 100 nm.

The invention relates the use of nano particle that are embedded into the implant in order to form the areas of inorganic, catalytic substance for improved biocompatibility of the material. The nano particles are made of catalytic material. The amount of particles added to the bulk material should be such that the average spacing between exposed particle falls into the ranges describe above for micro patterned surface coatings. The particles are mixed with the bulk material to be exposed on the surface of the implant. As the implant surface wear down the newly formed surface will present randomly arranged nano particle in the bulk material, throughout the life time of the implant.

In one embodiment of the material for implantation according to the invention, the inorganic, catalytic substance is chosen from the group comprising titanium dioxide, zirconium dioxide, palladium, gold and platinum.

In another embodiment of the material for implantation according to the invention, the inorganic, catalytic substance is the crystalline phase of titanium dioxide or zirconium dioxide.

In yet another embodiment of the material for implantation according to the invention, the at least one area of inorganic, catalytic substance comprised in the surface of the material for implantation is obtainable by a layer of titanium or zirconium patterned into an array of areas.

In still another embodiment of the material for implantation according to the invention, said material comprises a base material, which is chosen from the group comprising polymers, metals and ceramics and in yet another embodiment the base material is chosen from the group comprising polyurethane, polyethylene and silicone elastomer.

In one embodiment of the invention the material for implantation according to the invention, said material is a medical sensor, a drug delivery system, an orthopedic and reconstructive implant or an articulating surface.

In a second aspect of the present invention the object is fulfilled by a method of manufacturing a material for implantation according to the invention, characterised in that the inorganic, catalytic substance is added by chemical or physical deposition techniques.

In one embodiment of the method according to the invention the deposition techniques are sol-gel, metallorganic chemical vapour deposition, dc magnetron sputtering or radio frequency sputtering.

In a third aspect of the present invention the object of the invention is fulfilled by use of a material for implantation as a medical sensor, a drug delivery system, an orthopedic and reconstructive implant or an articulating surface.

DESCRIPTION OF THE DRAWINGS

FIG. 1. Chemiluminescent signal from the reaction of MCLA with superoxide produced by J774.1 A murine macrophages after stimulation by phorbol myristate acetate. A) Macrophages cultured on quartz petri dishes with different crystalline forms of titanium dioxide. B) Macrophages cultured on thermoset silicone polymer substrates with and without amorphous titanium oxide coatings. Error bars given as SEM.

DETAILED DESCRIPTION OF PREFERRED EMBODIMENTS

Figure 2:
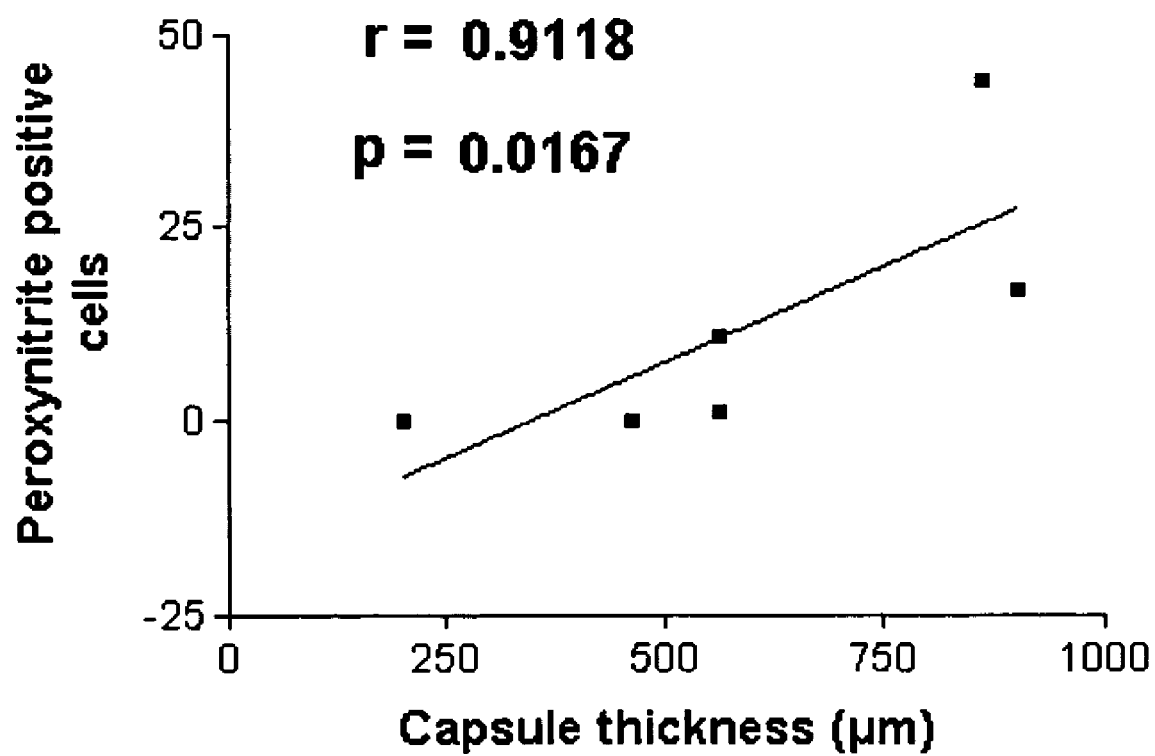
FIG. 2. Correlation between protein nitrosylation and synovial capsule thickness with implanted discs of 316L stainless steel in the suprapatellar pouch of arthritic Lewis rats. Implants were maintained for 28 days.

It has been known for decades that $TiO_2$ can act as a catalyst in reactions involving reactive oxygen species. Crystalline $TiO_2$ powder has been examined as a photocatalyst for the purification of water. Hydroxyl radicals that initiate oxidation of hydrocarbons to carbon dioxide, water and water-soluble organics are involved in these reactions. These findings indicate that titanium oxide can act as a catalyst in reactions involving free radical species.

Macrophages produce both superoxide and nitric oxide when stimulated. Polymorphonuclear leukocytes produce superoxide after stimulation. Superoxide undergoes a rapid reaction with superoxide dismutase to form hydrogen peroxide. Superoxide dismutase has a critical role in regulating reactive oxygen species concentrations. This regulatory process appears to be compromised, however, in tissues surrounding polyester implants (Glowinski, Farbiszewski et al. 1997). This is likely due to inactivation of the enzyme by the oxidative environment generated by the inflammatory response, thus compounding the deleterious accumulation of oxidant species in the vicinity of the implant.

In addition to superoxide, another reactive species, peroxynitrite, is a mediator in the inflammatory response. Peroxynitrite is formed by the reaction of superoxide with nitric oxide at near-diffusion limited rates which are several times faster than the reaction of superoxide with superoxide dismutase. Macrophages and cells from inflammatory exudates are suspected to produce peroxynitrite in vivo.

Peroxynitrite is a very reactive oxidant thought to play a role in inflammation. Peroxynitrite directly induces colonic inflammation in rats and has been demonstrated to be present in the inflamed guinea pig ileum. Peroxynitrite was found to be produced by acute inflammation from edema induced in hind paws of rats. This edema was inhibited by selective superoxide and nitric oxide inhibitors. Peroxynitrite has also been implicated in experimental autoimmune encephalomyelitis in mice. Proteins with tyrosine residues nitrosylated by peroxynitrite dramatically induced granulomas when injected into rabbits (personal communication, Dr. Harry Ischiropoulos).

Clinical studies also provide evidence that peroxynitrite is produced during inflammation. The blood serum and synovial fluid from patients with the inflammatory joint disease rheumatoid arthritis were found to contain 3-nitrotyrosine markers indicating peroxynitrite formation, while body fluids from normal patients contained no detectable 3-nitrotyrosine. Similarly, no 3-nitrotyrosine markers were detected in body fluids from patients with osteoarthritis, a largely non-inflammatory joint disease. Importantly, it has been reported that 3-nitrotyrosine markers for peroxynitrite were also observed at the interface membrane of hip implants suffering from aseptic loosening, which is characterized by local inflammation (Hukkanen, Corbett et al. 1997; Hukkanen, Corbett et al. 1998).

Furthermore, synthetic decomposition catalysts specific for peroxynitrite are being explored as a method of inhibiting damage induced by this potent reactive species (Misko, Highkin et al. 1998). Metalloporphyrin catalysts capable of breaking down peroxynitrite have been shown to have protective effects in animal models involving inflammatory states ranging from splanchinic artery occlusion and reperfusion, experimental autoimmune encephalomyelitis, endotoxin induced intestinal damage and carrageenan-induced pawedema. (Salvemini, Riley et al. 1999; Cuzzocrea, Misko et al. 2000). These results clearly indicate the potential therapeutic benefits of reducing cellular damage at site of the inflammatory response after implantation through catalytic breakdown of peroxynitrite.

Polyethylene implants coated with superoxide dismutase mimics have showed a notable decrease in the adverse foreign body response when measuring its thickness compared to uncoated controls (Udipi, Ornberg et al. 2000). This is consistent with the reported direct link between superoxide to the production of proinflammatory mediators, including cytokines, through two transcriptional activators, NF-κB and AP-1. These results indicate that species such as superoxide, a precursor of peroxynitrite, also plays a role in the inflammatory response to biomaterial surfaces.

Results of studies show that titanium is capable of enhancing the breakdown and inhibiting the reactivity of peroxynitrite (Suzuki and Frangos 2000). Titanium oxide was also shown to inhibit the nitration reactions of peroxynitrite at physiological pH levels compared to polyethylene. Titanium surfaces retained the ability to inhibit peroxynitrite while in the presence of 10% fetal bovine serum, fibrinogen and bicarbonate.

It has also been shown that zirconium also possesses the ability to inhibit peroxynitrite as well (Suzuki and Frangos 2000). Zirconium falls directly below titanium in the periodic table, thus both elements share similar chemical properties since both have the same outer electron configuration and form a stable $4^+$ ion. It was also found that palladium can inhibit the reactivity of peroxynitrite at physiological pH levels. Palladium, like titanium dioxide, has been used as an industrial catalyst for decades indicating that the catalytic properties of these materials may be responsible for their ability to inhibit peroxynitrite. Gold and platinum are also well known catalysts for many applications and have been shown to facilitate the decay of reactive oxygen species like peroxynitrite and superoxide.

The present invention is based on the hypothesis that the oxide surface layer of titanium implants plays a critical role as an inorganic catalyst which neutralizes reactive inflammatory mediators thus inhibiting the ability of these mediators to induce an inflammatory response. A biomaterial which could be given an inorganic catalytic surface layer similar to titanium could thus be imparted with the superior biocompatible properties of titanium. The patent is primarily based on the fact that the surface does not need to be completely covered with the catalytic compound to achieve the beneficial effects of the coating.

Surface treatments of biomaterials to enhance biocompatibility have been mostly directed toward modification of the chemical functional groups on the surface of addition of biomolecules to the surface. These functional groups of biomolecules are added in an attempt to modify blood compatibility, cell adhesion and protein adsorption. There are numerous methods used to modify materials in this manner. Among them are chemical surface reactions, surface layers grafted on by radiation of photografting, plasma deposition of chemical functional groups, self-assembling films, and surface-modifying components added during fabrication. These result in surfaces covered with alkyl, hydroxyl, phenol, fluoroalkyl or chemical functional groups. The underlying reasons for the biocompatibility of certain material have remained unanswered largely due to the emphasis on functional group modification as a way of improving biocompatibility.

Surface treatments that do not involve modification or addition of surface functional groups are limited. Ion beam implantation is used to modify a metal's hardness or corrosion resistance. Passivation is another method used to increase corrosion resistance by increasing the thickness of the metal oxide layer. Application of an inorganic catalytic layer to metallic or non-metallic materials has not yet been attempted.

The invention provides material for implantation, which comprises metallic and non-metallic base materials, which partially comprises an inorganic catalytic substance in the surface, which substance will serve as an inorganic catalyst to breakdown reactive inflammatory species. Titanium oxide films can be deposited onto various substrates, such as silicone elastomers. The titanium oxide films can also be applied to other polymers, metals and ceramics and can thus be used to coat non-biocompatible material with catalytic surface areas. Inorganic catalytic coatings of other materials can also be applied. Published experiments regarding zirconium and palladium (Suzuki and Frangos 2000), also lead to the suggestion that their oxides may also serve as potential inorganic catalysts for reactive inflammatory species.

Several methods to fabricate these coatings can be applied. Thin film oxide coatings are from 1 nm to 100 µm, typically <1 µm, in thickness and can be produced by chemical or physical vapor deposition techniques. The deposited films are directly after deposition mostly amorphous and can be crystallized under post-deposition thermal annealing. Physical vapor deposition techniques, such as radio frequency (r.f.) and d.c. magnetron sputtering are limited to the use of flat substrates. In r.f. sputtering, the material to be deposited is originally from a disk of the selected material (the target). The target is bombarded by Ar plasma to transfer material from the target to the substrate. This method results in uniform, flat stoichiometric films with controllable thickness. R.F. sputtering can be carried out at temperatures low enough to allow the films to be applied to polymers.

By varying the oxygen partial pressure during deposition, different oxidation states of $TiO_{2-x}$ will be deposited ranging from x=0–1.5. The oxides deposited will be amorphous for low substrate temperatures and crystalline for higher (>250° C.) substrate temperatures. Depending on the choice of the substrate, different crystallographic orientations can be induced in the films. For examples, glass substrates produce polycrystalline films while single crystal sapphire (oriented in the (001) direction, a=0.4759 nm) substrates produce oriented rutile films. By varying the thicknesses (2-200 nm) the final grain size can be controlled. Longer deposition result in larger grain sizes due to the prolonged exposure to high temperatures. By using such crystalline coatings we have found that the catalytic properties of the titanium oxide can be drastically improved compared to the amorphous phase. Such crystalline phases should be considered whenever possible.

Alternatively, chemical techniques involve a reaction between precursor compounds, such as in sol gel techniques or metallorganic chemical vapor deposition (MOCVD). Sol gel typically refers to the hydrolysis reaction of a metal alkoxide. The reaction sequence is complicated, but can be generally expressed by the below reaction, for a metal (z+ valence) isopropoxide and water:

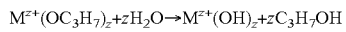

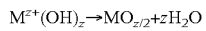

A substrate or shaped piece can be dipped into the alkoxide solution and then allowed to hydrolyze in a moist atmosphere. The coating thickness can be controlled by the number of times the piece is dipped into the solution, as well as the temperature and concentration. In MOCVD, the precursors are long chain organic molecules with a metal ion attached. An example are the metal tris(2,2,6,6,-tetramethyl-3,5-heptanedionates). The precursors are heated and the sublimated vapor is carried by argon gas to the reactor where the metal-lorganic vapor species deposits on a heated substrate and decomposes with oxygen introduced into the chamber to form an oxide film. The substrate need not be flat, but can be a shaped piece that is suspended in the reactor. The temperature of the precursors, the flow rate of the carrier gases and the deposition time control the film thickness.

The deposition techniques mentioned, but not limiting, have been selected to not only complement each other, but to examine the best deposition method for coating oxides on various industrially relevant polymers. The techniques are widely used by industry for metal, semiconductor and ceramic coatings. For some applications, curved surfaces may need to be coated. However, it is to be ascertained which technique, MOCVD or sol gel, would produce the most adherent coating on a curved surface. This is an example of how the techniques complement each other.

Silicone is a family of synthetic polymers derived from the reaction of elemental silicon with methyl chloride to form dimethyl cholorsilane. Hydrolysis with water generates a silicon backbone polymer chain. Polydimethylsiloxane is the most widely used form of silicone polymer and has been used both in silicone gels and as silicone elastomer (Silastic).

Due to the physical properties and ease of manufacturing of silicone elastomers, this polymer has served as a biomaterial for numerous medical devices including coverings for cardiac pacemaker leads, renal dialysis tubing, uterine rings, contact lenses, artificial heart valves, finger joint prostheses, and testicular and breast implants.

Silicone is therefore a good candidate as a base material to receive an inorganic catalytic surface coating to improve its biocompatibility and minimize the inflammatory response resulting from this material's implantation.

These coating methods can be applied to nearly any material to allow previously non-biocompatible materials to be accepted by the body. This opens and enormous range of base materials which can be used for implanted devices and greatly enhances the choices available in terms of physical properties. This coating method can be applied to any kind of material for implantation placed in the body including medical sensors, drug delivery systems, orthopedic and reconstructive implants.

We have surprisingly found that a surface modification does not need full coverage of the surface of an implanted biomaterial to serve the intended purpose. Instead significant biological effects may be obtained with only partial but well dispersed patches of such coatings. The distance between these patches should be in the same order of magnitude as a cell or smaller. This means that the distance between two adjacent patches should be less than 10 µm. The lower limit is set by fabrication considerations and how much non-covered area is needed to achieve the function of the base material or surface.

An example of such an application is an implantable sensor. The patches of the catalytic material, as described in this application, serve to reduce the adverse biological effects of the implanted device while the uncovered areas will provide the sensing surface of the sensor. The lower limits of the distance between two adjacent patches are set by the function of the sensor in this example while manufacturing considerations may be the limiting factor in other applications. In general the distance between two adjacent patches should preferably be larger than 10 nm.

For surfaces that are susceptible to wear another approach to create the catalytic properties of the surface of the material for implantation may be employed. A surface coating will under these circumstances only have a limited life span as the coating will wear off. An example of such an application is the articulating surface of a joint prosthesis. Polyethylene is a commonly used material in such surfaces. It is known that wear particles generated from such joint prostheses will cause inflammation and in some instances loosening of the prosthesis. This invention teaches that the adverse effects of such wear particles may be reduced by adding the catalytic substance throughout the base material, which is described in this patent, as minute suspended particles. These catalytic particles should be as small as possible for two reasons: Firstly the particles per se, if they become free and separated from the material, should not elicit inflammatory cells that ingest the particles. To avoid this, the particles should be less than 0.5 µm, but preferably as small as the size of the constituting molecules allows. The lowest achievable limit is therefore set to 1 nm. The particles should preferably have a size of 10-100 nm.

EXAMPLE 1

Experiments with Inorganic, Catalytically Coatings

Titanium dioxide coatings which have been sputter-coated onto glass and polymer substrates have been found to inhibit superoxide production in stimulated macrophages (FIG. 1). Interestingly, the anatase crystalline isoform of $TiO_2$ was more effective than the rutile isoform. With the use of quantitative photon counting microscopy, we are able to measure the chemiluminescent signal from MCLA (2-methyl-6-[p-methoxyphenyl]-3,7-dihydroimidazo[1,2-a]pyrazin-3-one) induced by production of superoxide from J774A.1 mouse macrophages stimulated with PMA (phorbol 12-myristate 13-acetate).

FIG. 2 demonstrates that peroxynitrite production correlates well with classical indicators of the foreign body response such as fibrotic capsule thickness. This result strongly supports our hypothesis that peroxynitrite levels (and the inability to degrade reactive oxygen species) reflect the degree of inflammation induced by a foreign body, and thus is an indicator of biocompatibility.

Figure 3:
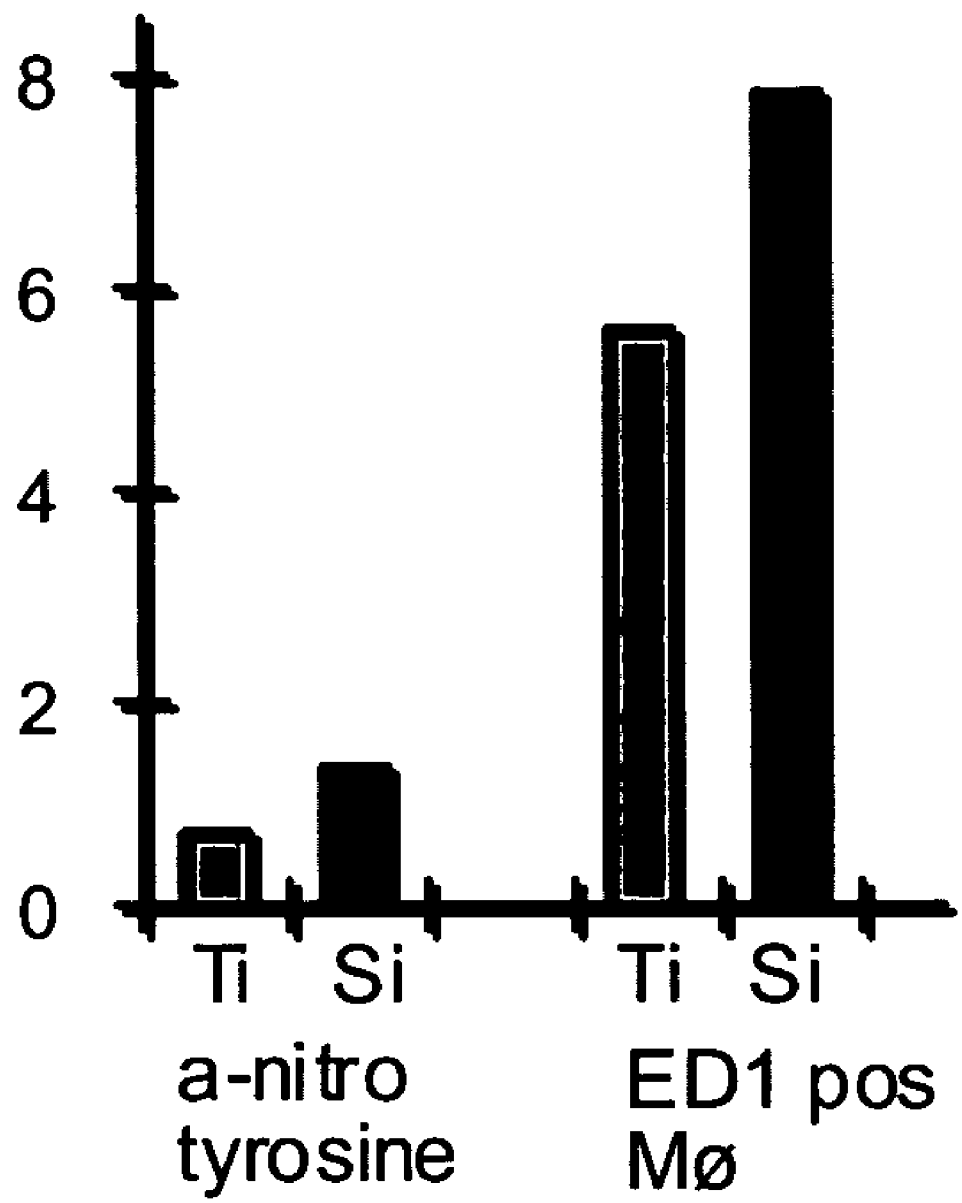
FIG. 3. Comparison of the tissue response as indicated by anti-nitrotyrosine staining and ED-1 positive cells to silicone elastomer versus titanium dioxide coated elastomer. Densities for nitrotyrosine positive cells as well as ED1 positive macrophages.

Preliminary experiments comparing the tissue response to silicone elastomer coated with titanium dioxide indicate that the coated material induces less inflammatory, ED1-positive cells as well as fewer cells positive for anti-nitrotyrosine staining when implanted in the rat abdominal wall for 28 days (FIG. 3).

EXAMPLE 2

Method of Manufacturing of Oxide Coated Silicone Elastomer Samples

Silicone elastomer was obtained of a thickness of 1 mm. Silicone was cut in circles about 5 cm in diameter. These circles were cleaned using acetone and ethanol in an ultrasonic bath and dried with clean flowing air. Animal experiments used circular samples, which were 5 mm in diameter and punched from the larger 5 cm silicone circles. These samples were then placed back in the holes of the original 5 cm silicone circle to facilitate deposition of the coating. The silicone was cleaned again using ethanol to rinse away any contaminants from the punching process. Copper rings were used to hold the silicone elastomer in place in the plasma sputtering chamber. A cleaned sputtering chamber with the appropriate target was used to deposit the coatings. Plasma power and argon pressure settings appropriate for the coating material was used to R.F. magnetron plasma sputter films of thickness ranging from 10 nm to 100 μm. Both sides of the samples were coated in this manner. After deposition the samples were stored in covered petri dishes until they were ready for use. They were sterilized using standard means.

In some instances, glass or quartz materials were used instead of silicone elastomer as the substrate material. In these cases, the glass was cleaned ultrasonically using acetone and ethanol and clean flowing air. Deposition occurred in a similar manner, except that adhesive tape was used to mount the samples instead of copper rings.

These experiments indicate that titanium oxide coatings can act as an inorganic catalyst to inhibit reactive oxygen species and downregulate the inflammatory response which results from the implantation of a biomaterial in the body. Reduction of the inflammatory response would serve to improve wound recovery around the site of implantation and increase the overall biocompatibility of an implant.

Evidence has been published, which indicate that zirconium and palladium also share these catalytic properties with titanium. Any material which possesses these catalytic properties and which can be coated onto surfaces through the processes described here could serve in a similar manner as titanium oxide coatings.

Such coatings can be applied to a variety of substrates thus imparting improved biocompatibility to materials lacking this critical property. The process of applying inorganic catalytic coatings can open a wide range of materials with different physical properties for use as implants, medical devices and any application which requires biomaterials with good biocompatibility.

REFERENCES

Albrektsson, T., P. I. Branemark, et al. (1983). "The interface zone of inorganic implants in vivo: Titanium implants in bone." *Annals of Biomedical Engineering* 11: 1-27.

Cuzzocrea, S., T. P. Misko, et al. (2000). "Beneficial effects of peroxynitrite decomposition catalyst in a rat model of splanchinic artery occulsion and reperfusion." *FASEB Journal* 14(N9): 1061-1072.

Glowinski, J., R. Farbiszewski, et al. (1997). "Activity and distribution of superoxide dismutase in the layers of polyester grafts." *European Surgical Research* 29: 368-374.

Hukkanen, M., S. Corbett, et al. (1997). "Aseptic loosening of total hip replacement. Macrophage expression of inducible nitric oxide synthase and cyclo-oxygenase-2, together with peroxynitrite formation, as a possible mechanism for early prosthesis failure." *Journal of Bone and Joint Surger*, British Volume 79(3): 467-474.

Hukkanen, M., S. A. Corbett, et al. (1998). "Nitric oxide in the local host reaction to total hip replacement." *Clinical Orthopaedics and Related Research* 352: 53-62.

Johansson, A; Lindgren, J U; Nord, C E; Svensson, O. (1999) Material and design in haematogenous implant-associated infections in a rabbit model. *Injury* 30(10):651-7.

Misko, T. P., M. K. Highkin, et al. (1998). "Characterization cytoprotective action of peroxynitrite decomposition catalysts." *Journal of Biological Chemistry* 273(25): 15646-15653.

Salvemini, D., D. Riley, et al. (1999). "Protective effects of a superoxide dismutase mimetic and peroxynitrite decomposition catalysts in endotoxin-induced intestinal damage." *British Journal of pharmacology* 127(N3): 685-692

Suzuki, R. and J. A. Frangos (2000). "Inhibition of inflammatory species by titanium surfaces." *Clinical Orthopaedics and Related Research* 372: 280-289.

Udipi, K., R. L. Ornberg, et al. (2000). "Modification of inflammatory response to implanted biomedical materials in vivo by surface bound superoxide dismutase mimics." *Journal of Biomedical Materials Research* 51(549-560).

The invention claimed is:

1. An implant comprising:
   a sensor having a permeable membrane; and
   a plurality of spaced apart patches of titanium dioxide disposed on the permeable membrane, each patch having a distance of separation from its nearest adjacent patch, the distance of separation being from about 10 nm to about 10 μm,
   wherein the permeable membrane allows the exchange of a molecule to be monitored by the sensor.

2. The implant of claim 1, wherein the spaced apart patches have a thickness of less than about 1 μm.

3. The implant of claim 1, wherein the spaced apart patches have a thickness of from about 1 nm to about 100 μm.

4. The implant of claim 1, wherein the implant comprises a material selected from the group consisting of polymers, metals, and ceramics.

5. The implant of claim 4, wherein the polymer is selected from the group consisting of polyurethane, polyethylene, and silicone elastomer.

6. The implant of claim 1, wherein the spaced apart patches are distributed on the permeable membrane.

7. The implant of claim 1, wherein the sensor is a glucose sensor.

* * * * *